United States Patent

Shaw, IV

[11] 4,043,324
[45] Aug. 23, 1977

[54] CHIROPRACTIC ANALYTIC TECHNIQUE WITH A LIQUID CRYSTAL SHEET

[76] Inventor: Alexander F. Shaw, IV, 329 E. 11th St., Davenport, Iowa

[21] Appl. No.: 657,914

[22] Filed: Feb. 13, 1976

[51] Int. Cl.² .............................................. A61B 10/00
[52] U.S. Cl. ..................................... 128/2 H; 128/68
[58] Field of Search .............. 128/2 H, 2 A, 2 R, 2 S, 128/68, 69

[56] References Cited

U.S. PATENT DOCUMENTS

| 2,532,915 | 12/1950 | Horner | 128/2 S |
| 3,306,282 | 2/1967 | Pierce | 128/2 H |
| 3,533,399 | 10/1970 | Goldberg | 128/2 R |
| 3,620,889 | 11/1971 | Baltzer | 128/2 H X |
| 3,661,142 | 5/1972 | Flam | 128/2 H |
| 3,830,224 | 8/1974 | Vanzetti et al. | 128/2 H |
| 3,847,139 | 11/1974 | Flam | 128/2 H |
| 3,998,210 | 12/1976 | Nosari | 128/2 H |

OTHER PUBLICATIONS

Crissey et al., "A New Technique... Skin Temperature Patterns", The Journal of Investigative Dermetology, May, 1964, pp. 89-91.

*Primary Examiner*—Robert W. Michell
*Assistant Examiner*—Lee S. Cohen
*Attorney, Agent, or Firm*—Henderson, Strom & Sturm

[57] ABSTRACT

A method of chiropractic analysis using a liquid crystal sheet. A liquid crystal sheet is placed over the back of a patient properly positioned upon a chiropractic adjustment table. The chiropractic doctor studies the color patterns of the sheet for the purpose of analysis and then administers the appropriate adjustment to the patient. Thereafter, the color patterns are again studied and additional adjustment made when appropriate.

7 Claims, 1 Drawing Figure

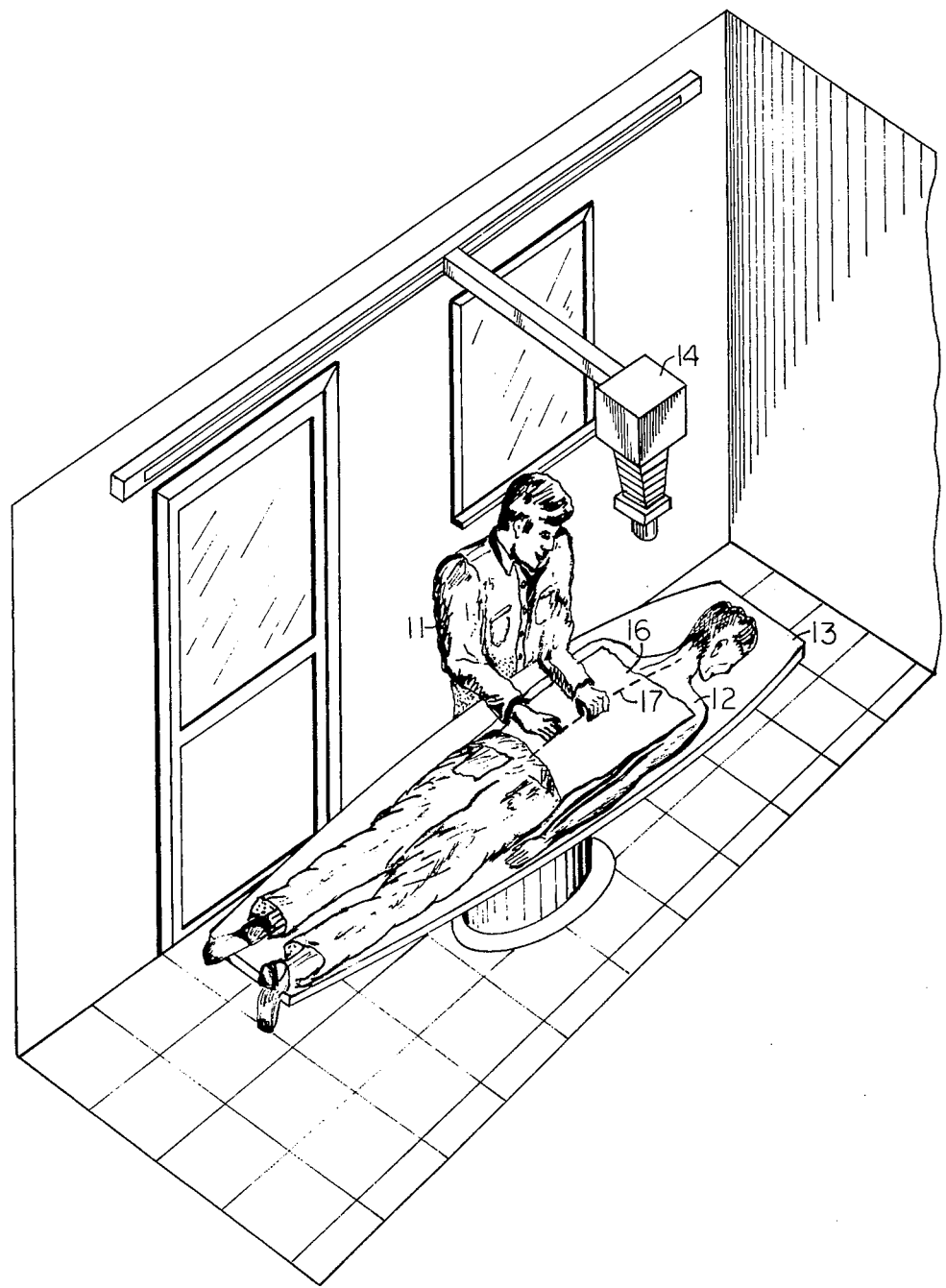

CHIROPRACTIC ANALYTIC TECHNIQUE WITH A LIQUID CRYSTAL SHEET

BACKGROUND OF THE INVENTION

This invention relates to medical analytic techniques. More particularly this invention relates to chiropractic methods of analysis and treatment.

The spine of the patient and areas of the body of the patient adjacent thereto are of central importance in chiropractic analysis. A lack of normal nerve function can result in a condition of ill health to the patient. Interference with the nerves and normal nervous transmission can be caused by situations of malpositioned contiguous vertebrae of the spine. These situations are known as subluxations and usually trigger inflammation reactions of the paravertebral structures resulting in vasodilation thereabout. These inflamed areas of the body usually exhibit both increased temperature and increased electrical conductivity.

Chiropractic treatment to correct a condition of ill health in a patient employs a specific adjustment of bodily structures. Most particularly, a chiropractic adjustment is administered at appropriate vertebral levels along the spine of the patient. Before an appropriate treatment may be administered, the patient must be examined and the alignment of the spine analyzed.

A number of techniques hae been developed for chiropractic analysis. The chiropractic doctor may use the technique of palpation, touching with the fingers the back of the patient over the spinous and transverse processes of the spine and areas adjacent thereto. Mechanical temperature sensing devices have also been developed which are placed against the back of the patient over the spinal area. Some of the temperature sensing devices take readings simultaneously from the areas on opposite sides of the line of the spinous processes and equidistant thereto. Infrared detectors of various kinds have also been used. Electrical devices have also been developed which measure the electrical conductivity of areas of the body and which are applied to take measurements along the spine of the patient. X-ray films of the spine may also be taken. By scanning the back of the patient along the spine using palpation, temperature measurement or conductivity measurement, the doctor may ascertain areas along the spine which merit closer examination. By then taking X-ray films of the spine or applying the other techniques, the doctor can locate the areas of trauma or position of subluxations along the spine and thereby determine the adjustment which is to be made.

The foregoing analytic process can be quite cumbersome. The separate devices which are used for temperature or conductivity measurement must be maneuvered into position for use and then removed so that other devices or techniques may be used. Although the results of several different techniques can be compared to more certainly obtain the correct analysis, this is made difficult by the fact that the different techniques cannot be performed simultaneously. Furthermore, the results of an adjustment cannot be ascertained until analytic procedures have been performed again, and additional adjustments cannot be performed as soon as they might be.

A further drawback of the foregoing analytic process is that the temperature and conductivity sensing devices take readings at a discrete point on the back of the patient. When the back of the patient is scanned, a series or line of point readings are taken. Palpation permits analysis of an area of the back which is greater than a mere point. However, and with the exception of infrared thermography, a very expensive technique involving large and cumbersome machinery, neither the sensing devices nor palpation give a simultaneous reading of the whole area of the back such that the interrelationships between different areas of the back and between the conditions thereof may be ascertained.

SUMMARY OF THE INVENTION

The chiropractic analytic technique employs a liquid crystal sheet. The patient is positioned upon a chiropractic adjustment table, and a camera is positioned over the patient. The liquid crystal sheet is placed over the patient's back, and the color patterns of the sheet convey temperature information and are recorded by the camera. The doctor may simultaneously scan the back of the patient by palpation directly through the liquid crystal sheet while studying the color patterns of the sheet. After the doctor has determined the appropriate adjustment to be made, the adjustment is administered to the patient either directly through the liquid crystal sheet or after the sheet has been removed.

It is an object of this invention to provide a method of chiropractic analysis which may be more efficiently administered, allowing the health needs of a greater number of patients to be attended to while increasing the accuracy of analysis and effectiveness of adjustment.

Another object of this invention is to provide a method of chiropractic analysis which permits the simultaneous use of palpation and temperature scanning techniques, thereby rendering chiropractic analysis and adjustment more efficient and accurate.

A further object of this invention is to provide a method of chiropractic analysis which provides a rapid feedback of the results of an adjustment whereby chiropractic treatment can be rendered more effective.

Yet another object of this invention is to provide a method of chiropractic analysis which may be readily recorded thereby aiding treatment of patients by providing more accurate records.

Still another object of this invention is to provide a method of chiropractic analysis which permits measurement and analysis of the condition of the whole area of the back of a patient at once.

These objects and other features and advantages of the chiropractic analytic technique with a liquid crystal sheet, which technique comprises this invention, will become readily apparent upon referring to the following description, when taken in conjunction with the appended drawing.

BRIEF DESCRIPTION OF THE DRAWING

The chiropractic analytic technique with a liquid crystal sheet is illustrated in the drawing wherein the figure is a perspective view showing the doctor using the technique while administering to a patient.

DESCRIPTION OF THE PREFERRED METHOD

Referring now to the drawing, the doctor 11 is shown administering to the patient 12. The patient 12 is positioned upon a chiropractic adjustment table 13 such that the doctor 11 has access to the back of the patient 12. A camera 14 is positioned directly over the patient 12. As shown, the camera 14 is pointed normal to the back of the patient 12 when the patient 12 is properly positioned for the technique of this invention.

A thin, flexible and elastic liquid crystal sheet 16 is placed over the back of the patient 12. A weak adhesive substance may be first applied to the back of the patient 12, e.g. spraying a fine mist of water thereon, such that the sheet 16 remains more securely upon the patient 12. The liquid crystal compounds employed in the sheet 16 are so combined as to display colors in a temperature range of from about 30° C to about 40° C, which range includes the normal range of body temperatures. The liquid crystals are encapsulated in the sheet 16. Reference is made to U.S. Pat. No. 3,620,889 for a description of liquid crystal sheets in general.

As shown in the drawing, the doctor 11 first performs an analytic procedure. After the sheet 16 has been placed upon the back of the patient 12, a color pattern is formed on the sheet by the liquid crystals responding to the different temperatures of the areas of the back. The camera 14 is actuated such that a record is made of the pre-treatment condition of the patient 12. The doctor 11 studies the temperature pattern, particularly along the line of the spine 17. Simultaneously the doctor 11 may palpate directly through the sheet 16 the back of the patient 12 along the spine 17, particularly in areas exhibiting high temperatures. The doctor 11 thereby ascertains the areas of trauma, locations of subluxations, areas of inflammation or other areas of temperature difference and decides upon the appropriate adjustment therefor.

The doctor 11 then adjusts the patient 12 directly through the sheet 16 or after the sheet 16 has been removed. A color pattern forms on the sheet 16 after the adjustment is administered, and the pattern provides a feedback to the doctor 11, informing him of the effectiveness of the adjustment. The camera 14 is actuated to record the color pattern. Again, the doctor 11 may palpate the patient 12 while studying the temperature pattern displayed by the sheet 16 and also while studying the photographic records of earlier temperature patterns. A series of adjustments and analyses may be performed and a record made thereof.

A plurality of sheets 16 may be employed with the method of this invention. One sheet 16 would display colors corresponding to the broad temperature range of from about 30° C to about 40° C. Different sheets 16, having color displays corresponding to narrower temperature ranges (sub-ranges) somewhere within the aforementioned broad temperature range may then be used at the discretion of the doctor 11 for more detailed analysis of temperature patterns for areas of the back of the patient 12 which merit closer study. The narrower temperature ranges of the sub-range sheets 16 span about 2° to 3° C instead of the 10° C of the broad range sheet 16.

The thinness, flexibility and elasticity of the sheet 16 allow it to conform closely to the shape of the back of the patient 12 thereby permitting an accurate display of the temperatures of the areas of the back. These same properties permit the doctor 11 to palpate and administer adjustments to the patient 12 directly through the sheet 16. Chiropractic analysis and treatment is rendered more accurate and effective because the doctor may combine temperature and palpation techniques of analysis and, subsequent to an adjustment, may use the rapid feedback information from the sheet 16 and photographic records. The condition of the whole area of the back of the patient 12 is viewed at once, thereby permitting more correct analysis and effective treatment. Thus it can be seen that the objects of this invention have been attained.

Although a preferred method has been disclosed herein, it is to be remembered that various modifications can be made thereto without departing from the full scope of the invention, as defined in the appended claims.

I claim:

1. A method of chiropractic analysis of a patient using a liquid crystal sheet, said method comprising:
    positioning the patient upon a chiropractic table such that the doctor with his hands may reach the back of the patient;
    placing the liquid crystal sheet over the back of the patient;
    detecting the temperature patterns of different areas of the back of the patient by ascertaining the color patterns displayed by the liquid crystal sheet thereby to determine areas of trauma;
    palpating the back of the patient, the fingers of the doctor pressing through the liquid crystal sheet and against the body of the patient, thereby to determine areas of trauma; and
    adjusting the patient, the hands of the doctor pressing through the liquid crystal sheet and against the back of the patient to administer a chiropractic adjustment, the chiropractic adjustment being selected to treat the determined areas of trauma.

2. The method of chiropractic analysis of a patient using a liquid crystal sheet, as recited in claim 1, and further wherein the step of detecting the temperature patterns includes ascertaining colors corresponding to temperatures within the range of normal skin temperatures.

3. The method of chiropractic analysis of a patient using a liquid crystal sheet, as recited in claim 1, and further comprising the step of detecting, after adjusting the patient, the temperature pattern of different areas of the back of the patient by ascertaining the color patterns displayed by the liquid crystal sheet, thereby to determine the effectiveness of the adjustment.

4. The method of chiropractic analysis of a patient using a liquid crystal sheet, as recited in claim 3, and further comprising recording the temperature patterns of different areas of the back by photographing the color patterns displayed by the liquid crystal sheet subsequent to adjusting the patient.

5. The method of chiropractic analysis of a patient using a liquid crystal sheet, as recited in claim 1, and further comprising the recording of temperature patterns of different areas of the back by photographing the color patterns displayed by the liquid crystal sheet prior to adjusting the patient.

6. The method of chiropractic analysis of a patient using a liquid crystal sheet, as recited in claim 1, and further wherein the step of detecting the temperature patterns includes ascertaining colors corresponding to temperatures within the range from about 30° C to about 40° C.

7. The method of chiropractic analysis of a patient using a liquid crystal sheet, as recited in claim 6, and further wherein the step of detecting the temperature patterns includes replacing the liquid crystal sheet with a sub-range liquid crystal sheet, and detecting the temperature patterns of different areas of the back of the patient by ascertaining colors displayed by said sub-range sheet corresponding to temperatures within about a 3° C range within said range from 30° C to 40° C.

* * * * *